(12) United States Patent  (10) Patent No.: US 7,663,495 B2
Haque et al.  (45) Date of Patent: Feb. 16, 2010

(54) VIGILANCE MONITORING TECHNIQUE FOR VEHICLE OPERATORS

(75) Inventors: Amanul Haque, State College, PA (US); Amit V. Desai, Urbana, IL (US)

(73) Assignee: The Penn State Research Foundation, University Park, PA (US)

( * ) Notice: Subject to any disclaimer, the term of this patent is extended or adjusted under 35 U.S.C. 154(b) by 375 days.

(21) Appl. No.: 11/548,868

(22) Filed: Oct. 12, 2006

(65) Prior Publication Data

US 2007/0080816 A1  Apr. 12, 2007

Related U.S. Application Data

(60) Provisional application No. 60/725,822, filed on Oct. 12, 2005.

(51) Int. Cl.
*G08B 23/00* (2006.01)
(52) U.S. Cl. .................. 340/576; 340/575; 340/439; 180/272; 701/1
(58) Field of Classification Search ............ 340/576, 340/575, 439, 425.5, 426.15; 180/272; 701/1, 701/301
See application file for complete search history.

(56) References Cited

U.S. PATENT DOCUMENTS

| | | | |
|---|---|---|---|
| 3,788,357 A | 1/1974 | Welk, Jr. | |
| 4,564,833 A | 1/1986 | Seko et al. | |
| 4,594,583 A | 6/1986 | Seko et al. | |
| 4,604,611 A | 8/1986 | Seko et al. | |
| 5,717,606 A * | 2/1998 | Hara et al. | 701/44 |
| 5,798,695 A | 8/1998 | Metalis et al. | |
| 5,813,993 A | 9/1998 | Kaplan et al. | |
| 6,061,610 A * | 5/2000 | Boer | 701/1 |
| 6,335,689 B1 * | 1/2002 | Mine | 340/576 |
| 6,756,903 B2 | 6/2004 | Omry et al. | |
| 2004/0209594 A1 | 10/2004 | Naboulsi | |

* cited by examiner

*Primary Examiner*—Anh V La
(74) *Attorney, Agent, or Firm*—McKee, Voorhees & Sease, P.L.C.

(57) ABSTRACT

A vigilance monitoring system to determine the alertness of a driver of a vehicle. The system uses one or multiple sensors located at the driver-vehicle interface (steering wheel, accelerator, brakes). The sensor monitors the magnitude and frequency of the force (or displacement) exerted by a driver at the driver interface. A time derivative of the force or displacement profile is created. The variability of the time derivative of the force/displacement data from the general trend of the data as obtained by an optimized moving average of the data. An intelligent control system measures the variability and compares with an alertness rating scale to determine the alertness score of the driver and issue warning signals and actions as appropriate.

20 Claims, 9 Drawing Sheets

|  | Driver 1 | | Driver 2 | | Driver 3 | |
|---|---|---|---|---|---|---|
|  | Alert | Drowsy | Alert | Drowsy | Alert | Drowsy |
| 1. | 8.98E-02 | 2.13E-02 | 1.05E-01 | 2.97E-02 | 2.71E-01 | 2.52E-02 |
| 2. | 1.84E-01 | 3.37E-02 | 3.78E-02 | 9.11E-03 | 1.18E-01 | 9.90E-02 |
| 3. | 1.67E-01 | 1.24E-01 | 3.42E-02 | 7.37E-02 | 2.47E-01 | 9.83E-02 |
| 4. | 6.81E-02 | 1.40E-02 | 3.11E-02 | 9.11E-03 | 1.86E-01 | 1.05E-01 |
| 5. | 3.59E-02 | 8.90E-03 | 4.66E-02 | 9.11E-03 | 1.72E-01 | 3.43E-01 |
| Average | 1.09E-01 | 4.04E-02 | 5.09E-02 | 2.61E-02 | 1.99E-01 | 1.34E-01 |

Fig. 3

|  | Driver 1 | | Driver 2 | | Driver 3 | |
|---|---|---|---|---|---|---|
|  | Alert | Drowsy | Alert | Drowsy | Alert | Drowsy |
| 1. | 8.39E-03 | 3.98E-04 | 7.85E-04 | 8.58E-04 | 9.47E-02 | 4.82E-04 |
| 2. | 3.06E-02 | 1.03E-03 | 1.31E-03 | 8.67E-05 | 1.66E-02 | 1.06E-02 |
| 3. | 2.14E-02 | 1.23E-02 | 1.04E-03 | 6.11E-03 | 7.48E-02 | 1.04E-02 |
| 4. | 3.62E-03 | 1.91E-04 | 7.53E-04 | 8.67E-05 | 3.82E-02 | 9.91E-03 |
| 5. | 1.08E-03 | 9.03E-05 | 1.72E-03 | 8.67E-05 | 2.90E-02 | 1.30E-01 |
| Average | 1.30E-02 | 2.81E-03 | 2.92E-03 | 1.45E-03 | 5.07E-02 | 3.23E-02 |

Fig. 4

|  | Driver 1 | | Driver 2 | | Driver 3 | |
|---|---|---|---|---|---|---|
|  | Alert | Drowsy | Alert | Drowsy | Alert | Drowsy |
| 1. | 2.27E-02 | 6.09E-03 | 2.67E-02 | 8.45E-03 | 1.36E-01 | 4.23E-03 |
| 2. | 5.00E-02 | 8.85E-03 | 9.93E-03 | 2.00E-03 | 2.97E-02 | 2.42E-02 |
| 3. | 3.67E-02 | 1.73E-02 | 8.84E-03 | 1.79E-02 | 8.88E-02 | 3.03E-02 |
| 4. | 1.56E-02 | 4.60E-03 | 5.33E-03 | 2.00E-03 | 6.58E-02 | 2.16E-02 |
| 5. | 9.02E-03 | 3.33E-03 | 1.11E-02 | 2.00E-03 | 4.38E-02 | 8.97E-02 |
| Average | 2.68E-02 | 8.03E-03 | 1.24E-02 | 6.48E-03 | 7.28E-02 | 3.40E-02 |

Fig. 5

|  | Simulation for estimating noise | Simulation for estimating the effect of external vibrations | Deviation Data from a driver (lowest among the three) | Driver No. |
|---|---|---|---|---|
| $\sigma$ | 0.0093 | 0.0019 | 0.0261 | 2 |
| $\Psi$ (from moving average) | 3.5758E-06 | 8.2129E-05 | 1.45E-03 | 2 |
| $\Psi$ (from deviation from square wave) | 6.3708E-04 | 1.4E-03 | 6.48E-03 | 2 |

| Alertness Rating | Average PSD/SI for 11 Data Sets |
|---|---|
| 10 | 3000-1000 |
| 9 | 1000-500 |
| 8 | 500-200 |
| 7 | 200-50 |
| 6 | 50-10 |

Fig. 12

VIGILANCE MONITORING TECHNIQUE FOR VEHICLE OPERATORS

CROSS-REFERENCE TO RELATED APPLICATIONS

This application claims priority under 35 U.S.C. §119 to U.S. Provisional Patent Application No. 60/725,822, filed Oct. 12, 2005, herein incorporated by reference in its entirety.

BACKGROUND OF THE INVENTION

Impairment of alertness in vehicle and machinery operators poses a danger not only to themselves but also often to the public at large. Thousands of deaths and injuries result each year that are fatigue related. Moreover, the financial costs as a result of the injuries and deaths are prohibitive. As a result, significant efforts have been made in the area of vigilance monitoring of the operator of a vehicle to detect the decrease in attention of the operator and to alert her/him.

Existing driver vigilance monitoring techniques fall within the following broad classes: (1) image acquisition and processing of facial features such as eye and head movements; (2) image acquisition and processing of road lane maintaining capability and (3) monitoring of the physiological responses of the body while driving.

There are several limitations with the existing technologies. Although the most accurate of the vigilance monitoring techniques, monitoring physiological responses of the body like EEG and ECG, are intrusive, expensive and can distract or cause annoyance to the driver. Moreover, lane tracking methods require visible lane markings and even if present are significantly impaired by snow, rain, hail, and/or dirt existing on the road. Nighttime and misty conditions are also impairments. Image processing techniques used to track eyes and head patterns to track lane maintaining capability necessarily require expensive (both cost and computational requirement-wise) hardware to operate and are highly dependent on factors such as, the relative position of the driver's head with respect to the sensors, illumination, and facial features and/or mental state of the driver, whether happy, anxious, or angry. Each of these indicators suffers from a relatively low probability of detecting drowsiness. Many of the measurements for indicating drowsiness do not adequately represent the responsiveness of the driver because of such influences as road conditions, patterns and vehicle type. Moreover, the cost for these techniques is often prohibitive. Even yet, more often than not, the existing techniques detect drowsiness when it may be too late for accident prevention purposes.

Therefore, there has been a longstanding and continuing need for a system and method that detects drowsiness using parameters that are independent of the driving environment, such as traffic, landscape, weather, darkness, road conditions, patterns and vehicle type. Additionally, there is also a need for a driver vigilance monitoring system and method that detects drowsiness with very low false alarm and miss-rates without being intrusive, distractive to the driver and/or prohibitive in cost.

BRIEF SUMMARY OF THE INVENTION

Therefore it is a primary object, feature and advantage of the present invention to improve over the present state of the art by providing a vigilance monitoring system and method for detecting loss of alertness of a driver independent of the driving environment. Instead of interrogating the driver (physically or graphically) or the vehicle, the present invention interrogates the driver-vehicle interface, such as the steering wheel and the gas pedal. The core component of the invention is the concept of detecting driver/operator alertness by monitoring the magnitude and frequency of the force (and or displacement as in steering wheel rotation or accelerator depression) imparted by a driver at the vehicle interfaces. The time series data of operator imparted displacement or force is then differentiated one or more times to obtain the first, second, third order time derivatives or a time derivative profile. Such time derivatives are substantially independent of the driving environment and are distinctive for determining different levels of driver alertness when compared against a general trend of the time derivative of force or displacement profile.

It is a still further object, feature or advantage of the present invention to provide a driver vigilance monitor for monitoring driver alertness and/or drowsiness.

Another object, feature or advantage of the present invention is to provide a driver vigilance monitor wherein a force and/or a displacement sensor is positioned at a driver-vehicle interface, such as the steering wheel, accelerator or brake pedal.

Still another object, feature or advantage of the present invention is to provide a driver vigilance monitor wherein a force/displacement sensor is installed on both the accelerator, steering wheel and/or brake pedal to increase the probability of drowsiness detection.

Yet another object, feature or advantage of the present invention is to provide a driver vigilance monitor wherein the sensors monitor a physical characteristic of the driver, such as force or displacement applied by the driver to the driver-vehicle interface.

A further object, feature or advantage of the present invention is to provide a driver vigilance monitor wherein an intelligent control is operatively connected to the sensor.

Yet another object, feature or advantage of the present invention is to provide a driver vigilance monitoring system wherein the sensor for acquiring data from the vehicle-driver interfaces is a commercially available force or displacement sensor.

Still another object, feature or advantage of the present invention is to provide a driver vigilance monitor wherein an intelligent control computes one or higher order time derivatives of the force or displacement data.

Yet another object, feature or advantage of the present invention is to provide a driver vigilance monitor wherein a general trend is created from the time derivative of force or displacement data profile using a fixed moving average.

A further object, feature or advantage of the present invention is to provide a driver vigilance monitor wherein a general trend is created from the time derivative data of force or displacement data profile using a dynamic moving average.

A still further object, feature or advantage of the present invention to provide a driver vigilance monitor wherein a general trend is created from the time derivative profile using the most dominant frequency of a Discrete Fourier Transform (DFT) to determine the number of points for computing the moving average.

Yet another object, feature or advantage of the present invention to provide a driver vigilance monitor wherein the 'spikiness index' (or Fourier analysis or Power Spectral Density) of the time derivative of force or displacement data is used to determine the level of drowsiness of the driver.

Another object, feature or advantage of the present invention is to provide a driver vigilance monitor wherein the deviation of the time derivative of force or displacement data profile from the general trend is used to determine a 'spikiness index'.

Still another object, feature or advantage of the present invention is to provide a driver vigilance monitor wherein the 'spikiness index' measures local deviation of the time derivative of force or displacement data profile from the general trend.

Yet another object, feature or advantage of the present invention is to provide a driver vigilance monitor wherein the 'spikiness index' is used to assess the driver's vigilance by detecting drowsiness.

A further object, feature or advantage of the present invention is to provide a driver vigilance monitor wherein the 'spikiness index' is independent of the driving environment, such as traffic, landscape, weather, darkness, road conditions, road patterns and vehicle type.

A still further object, feature or advantage of the present invention to provide a driver vigilance monitor wherein the time derivative of force or displacement data profile and resulting 'spikiness index' requires minimum computational power and data processing time as no image processing requirement is required.

A still further object, feature or advantage of the present invention to provide a driver vigilance monitor wherein the time derivative of force or displacement data profile and resulting 'spikiness index' is distinctive for varying levels of alertness.

Another object, feature or advantage of the present invention is to provide a driver vigilance monitor having a neural network model for learning the driving characteristics of an alert driver for comparing against subsequent levels of alertness for the driver.

Another object, feature or advantage of the present invention is to provide a driver vigilance monitor that measures the alertness of the driver on a 1-10 alertness rating scale (with 10 as very alert and 1 as very drowsy state) based on the various levels of spikiness index, the power spectral density or an algorithm that measures variability in a time series data.

A still further object, feature or advantage of the present invention is to provide a driver vigilance monitor that measures the alertness of the driver on a 1-10 alertness rating scale from both the data from the steering wheel and the accelerator and then warn the driver only when both show lowered level of alertness.

Another object, feature or advantage of the present invention is to provide a driver vigilance monitor that warns the driver in the early stages of drowsiness and reduce control or force the driver to stop the vehicle for dangerously low alertness levels.

Still another object, feature or advantage of the present invention is to provide a driver vigilance monitor having a low unit, operation and data processing cost.

Yet another object, feature or advantage of the present invention is to provide a driver vigilance monitor that is easily installed by car manufacturers without affecting the functionality of the vehicle.

One and/or more of these and other objects of the invention will become apparent from the specification and claims that follow.

According to one aspect of the present invention, a vigilance monitoring system for alerting a driver of a vehicle upon detecting a state of drowsiness by calculation of a deviation between a time derivative of force and/or displacement exerted by the driver on a driver-vehicle interface and a moving average for the time derivative of force and/or displacement to thereby quantify the state of drowsiness of the driver independent of conditions inside and outside the vehicle is disclosed. The system includes a sensor connected to at least one driver-vehicle interface to monitor force on and/or displacement of the driver-vehicle interface. The system also includes an intelligent control in communication with the sensor as well as a time derivative profile modeled from the time derivative of force and/or displacement using the intelligent control. Included also is a general trend modeled from the moving average of the time derivative of force and/or displacement using the intelligent control. In addition, the system includes a spikiness index defined by a degree of deviation between the time derivative profile and the general trend to thereby quantify the state of drowsiness of the driver independent of conditions inside and outside of the vehicle.

According to another feature of the present invention, the driver-vehicle interface is an accelerator and/or a steering wheel.

According to another feature of the present invention, the time derivative profile is modeled from a time derivative of force on the accelerator using the intelligent control.

According to another feature of the present invention, the moving average is an optimized moving average calculated by a discrete Fourier transform to identify a dominant frequency to thereby assist estimation of an optimum number of points.

According to another feature of the present invention, the moving average is a dynamic moving average calculated using a dynamic number of points to approximate the time derivative profile with a plurality of square waves.

According to another feature of the present invention, the intelligent control alerts the driver of drowsiness upon detection of a decrease in the spikiness index relative to previous levels.

According to another feature of the present invention, a warning system in communication with the intelligent control, the warning system having an alert tone for notifying the driver of drowsiness.

According to another feature of the present invention, a neural network for learning a driving characteristic of the driver while in a state of alertness and detecting a state of drowsiness upon departure from the driving characteristic of the driver in the state of alertness.

According to another aspect of the present invention, a method for monitoring and alerting a driver of drowsiness is disclosed. The method includes monitoring an input from the driver on at least one driver-vehicle interface using a sensor as well as calculating a time derivative of the input at the sensor using an intelligent control. The method also includes generating a moving average for the time derivative of the input at the sensor using the intelligent control in addition to comparing a deviation between the time derivative of the input at the sensor and the moving average for characterizing drowsiness of the driver independent of road conditions or vehicle behavior. The method includes as well alerting the driver of drowsiness upon detection of a decrease in the deviation between the time derivative of the input at the sensor and the moving average.

According to another feature of the present invention, the intelligent control further comprises a memory and computational processing chip for storing and processing the input from the driver at the driver-vehicle interface.

According to another feature of the present invention, formulating a spikiness index or a power spectral density representing deviations between the time derivative of the input at the sensor and the moving average.

According to another feature of the present invention, using the spikiness index and/or power spectral density for detecting drowsiness in the driver.

According to another feature of the present invention, using a computer of the vehicle for the intelligent control.

According to another aspect of the present invention, a method for monitoring and alerting a driver of drowsiness in real-time comprising detecting a decrease in a deviation between a time derivative of an input by a driver at a sensor on a vehicle-driver interface and a moving average of the time derivative is disclosed.

According to another feature of the present invention, an intelligent control in communication with the sensor positioned on an accelerator for recording a force exerted by the driver on the accelerator.

According to another feature of the present invention, monitoring the sensor positioned on a steering wheel for recording a radial displacement of the steering wheel by the driver.

According to another aspect of the present invention, a vigilance monitoring system for alerting a driver of a state of drowsiness using a spikiness index defined by a deviation between a time derivative of displacement of a driver-vehicle interface and a moving average of the time derivative of displacement is disclosed. The system includes a sensor connected to the driver-vehicle interface and in communication with an intelligent control and a decrease in the spikiness index relative to previous levels of the spikiness index monitored by the intelligent control to thereby assist detection of drowsiness.

According to another feature of the present invention, the deviation between the spikiness index is independent of road conditions, road patterns and vehicle behavior.

According to another feature of the present invention, the state of drowsiness is detected by comparing the spikiness index to an alertness rating scale to determine an alertness score of the driver.

According to another feature of the present invention, the moving average of the time derivative of displacement is an optimized moving average for early detection of the state of drowsiness.

BRIEF DESCRIPTION OF THE DRAWINGS

FIG. 2A-B is a block diagram describing the operation of the present invention.

DETAILED DESCRIPTION OF THE INVENTION

The present invention relates to a vigilance monitoring system for measuring a driver's level of alertness. That which is disclosed herein is merely exemplary or representative of the present invention. The present invention is not to be limited to the specific disclosure provided herein.

Vigilance Monitoring Technique

Figure 1:
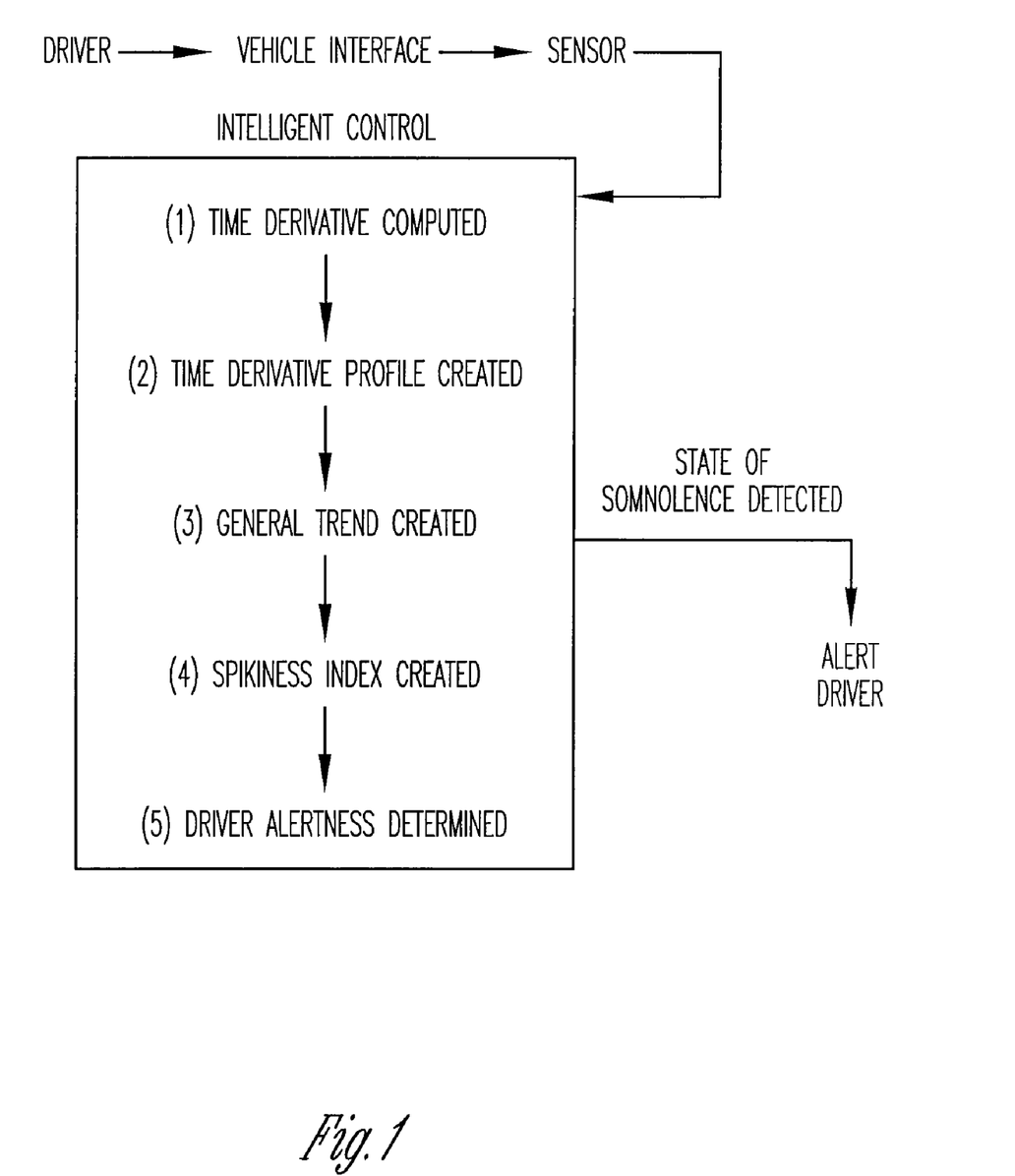
FIG. 1 is a flow chart of the present invention.

As shown in FIG. 1, the present driver vigilance monitoring technique monitors the time derivatives of the force and/or displacement profile of the driver's contact with accelerator and/or other driver-vehicle interface, such as the steering wheel and brake to monitor the alertness of the driver. A sensor in the preferable form of a force and/or displacement sensor is attached to the accelerator and steering wheel; the accelerator and steering wheel being the preferred driver-vehicle interfaces to monitor. The force sensor is in form of a thin polymer foil attached to the accelerator pedal, which makes the system non-intrusive to the driver and allows data acquisition and processing to be conducted in real-time. A position sensor such as an angular displacement rate sensor (Gyroscope) is attached to the steering wheel. The sensors operate to capture the driver's interaction with the accelerator and steering wheel, both of which are mandatory interactions for driving a vehicle. The effectiveness of the technique therefore depends on the resolution and ruggedness of the force and displacement sensors. The system is relatively low-cost since the sensors and other hardware are inexpensive and data processing requirements are minimal. It is also very easy to install and perform maintenance. The cost of the system becomes an important concern in the automobile industry where drivers are reluctant to pay a lot for additional features like vigilance monitoring.

Figure 7:
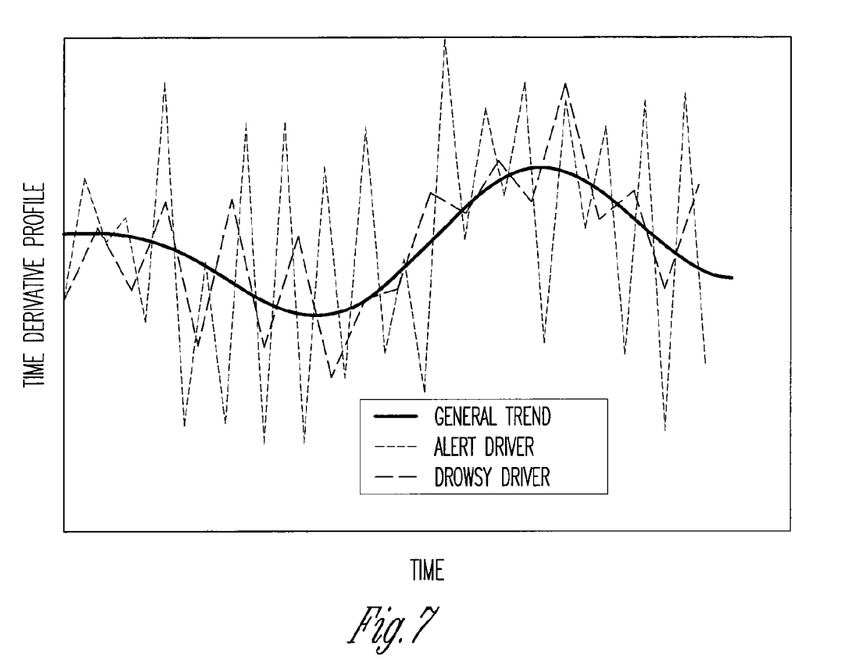
FIG. 7 is a plot of the time derivative profile for the present invention.

The intelligent control is used to capture the driver's interaction with the accelerator and steering wheel. The intelligent control may be an onboard computer of the vehicle or a central processing unit adapted for onboard configuration within the vehicle. The driver's interaction with the accelerator and steering wheel is recorded and stored in the control unit as time series data or data recorded with a time signature. The intelligent control is also configured to compute one or higher order time derivatives of the time series data from the sensor, usually recorded in terms of voltage. Though the magnitude and frequency of force and/or displacement and its variation depend on many parameters like vehicle type, physical characteristics of the driver, road patterns, external environmental conditions, the time derivatives of the force and/or displacement remove these various factors and only reflect the driver's responsiveness to any event while driving. Also, the deviation from general trend is used to determine the alertness, which in turn minimizes the influence of the above mentioned factors. To illustrate the proposed driver vigilance monitoring concept, a plot of the time derivative profile (time derivative of force) of driver contact with gas pedal is shown in FIG. 7. The general trend in the plot indicates the variation due to changes in road and external conditions. Over this trend the derivative of the force, exerted by an alert and a drowsy driver, on the gas pedal is superimposed. The time derivative profile for an alert driver has higher amplitudes and also frequency as compared to a drowsy driver; this correlation is depicted in FIG. 7.

Figure 8:
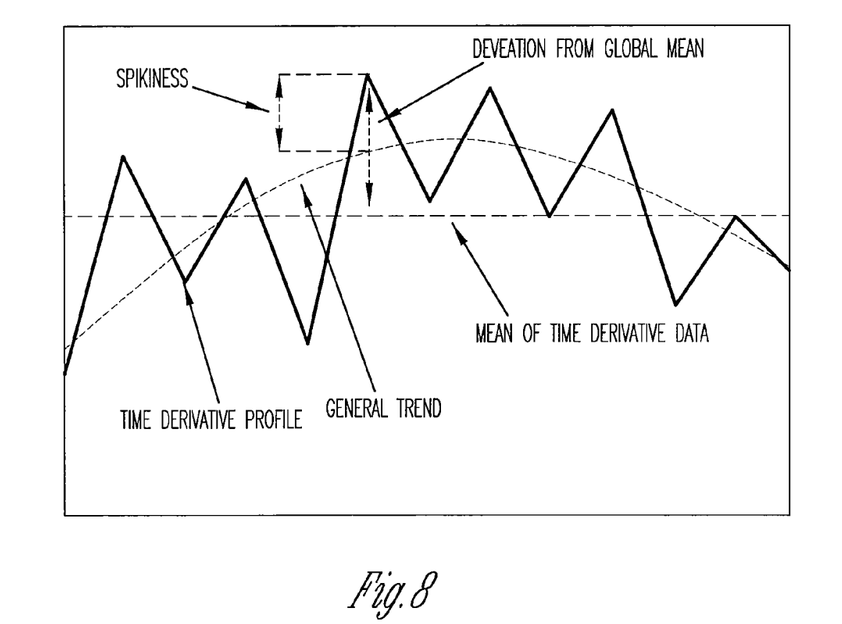
FIG. 8 is a plot of the 'spikiness index' for the present invention.

The time derivative profile computes what is known mathematically as "Jerk", or the rate of change of acceleration, or the third derivative of position with the respect to time. Jerk is a vector but may also be used loosely as a scalar quantity. Jerk encapsulates both the magnitude and frequency of force, so the force data from the sensor can be represented as a sum of sine functions. Accordingly, where f is the force, A is the amplitude and ω is the frequency, then jerk, J, is given by the amplitude of jerk. Thus, jerk is the product of amplitude and frequency of the force and representative of the magnitude and frequency of force and/or displacement data. A jerk profile over time or the time derivatives of the force and/or displacement data is recorded using the intelligent control. A general trend is fit to the time derivative profile using the intelligent control, as well. Deviations of the time derivative profile from the general trend are monitored in real-time by the intelligent control and are represented by a "spikiness index" and/or a Power Spectral Density (PSD), where the PSD describes how the power (or variance) of a time series is distributed with frequency. By definition, the "spikiness index" measures the local deviation of the time derivative profile from the general trend. This concept is illustrated in FIG. 8, where the time derivative profile is plotted versus time. The dashed straight line is the mean of the data and the dotted line represents the general trend. Generally for calculating standard deviation, the variation from the mean is estimated. In order to estimate the spikiness index, the variation from the general trend is computed; this is equivalent to calculating the 'local deviation'. Hence the 'spikiness index' represents the variations (spikes) from the general trend and the amplitude of the spikes will be used to estimate the alertness of the driver. As explained previously, the spikiness index (as opposed to standard deviation from mean) is a good indicator of the alertness since it measures the deviation from the general trend and hence takes into account the effect of extraneous parameters like physique of driver and road conditions and patterns. The details of the estimation of spikiness index will be discussed in a later section. Therefore, subsequent drop-offs or decreases in spikiness index are indicative of the driver entering a state of somnolence or having an impaired alertness. The intelligent control alerts the driver that a state of somnolence has been detected if a drop-off or decrease in the spikiness index is detected. Accordingly, deviation of the time derivative profile from the general trend of time derivative profile will be used to estimate the vigilance of the driver.

As discussed previously, the spikiness index measures local deviation from the general trend instead of measuring the deviation from a global average like mean. This concept is illustrated in FIG. 8, where the time derivative profile is plotted versus time. The dashed straight line is the mean of the data and the dotted line represents the general trend. For calculating standard deviation, the variation from the mean is estimated. In order to estimate the spikiness index, the variation from the general trend is computed; this is equivalent to calculating the 'local deviation'. Hence, the 'spikiness index' represents the variations (spikes) from the general trend where the amplitude of the spikes is used to estimate the alertness of the driver. The spikiness index (as opposed to standard deviation from mean) is a good indicator of the alertness since it measures the deviation from the general trend without effect of extraneous parameters like physique of driver and road conditions and patterns.

If the intelligent control detects a state of somnolence in the driver the intelligent control than alerts the driver. The alert system could use the preexisting onboard computer of the vehicle to alert the driver using the radio, preexisting alarms tones for the seatbelt or door ajar detection systems. Other alert systems such as an alarm with audible and visual displays cold be wired to the intelligent control to alert the driver of somnolence. The warning system may also have a vibration member for vibrating a vehicle seat, vehicle-driver interface, and/or an actuator for actuating a hazard light until vehicle is stopped or driver is alert. For dangerously low alertness levels, the intelligent control can actuate the hazard lights so that the only way the driver can stop it is by stopping the vehicle.

Data Acquisition Setup

Figure 2A:
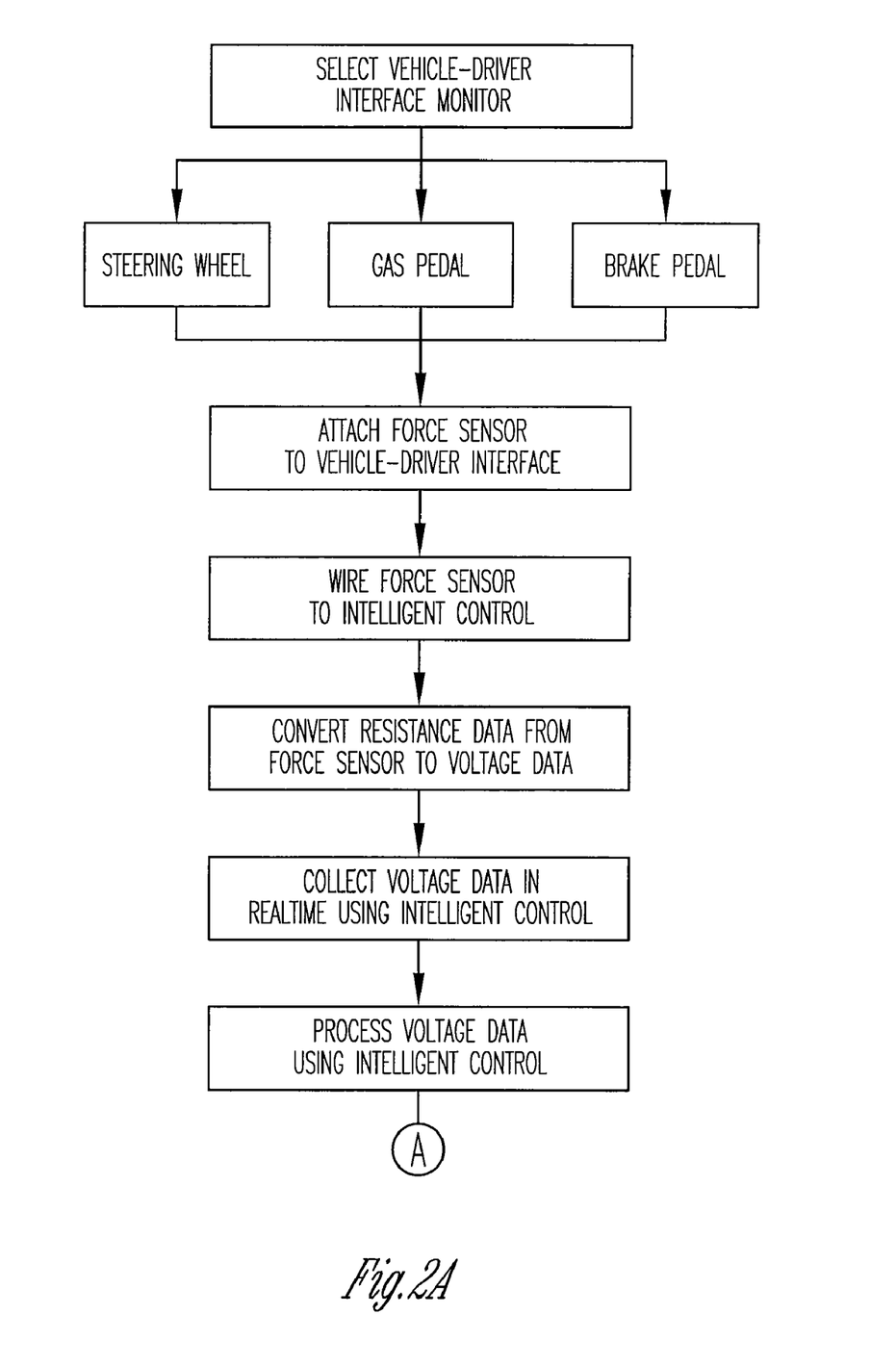
Figure 2B:
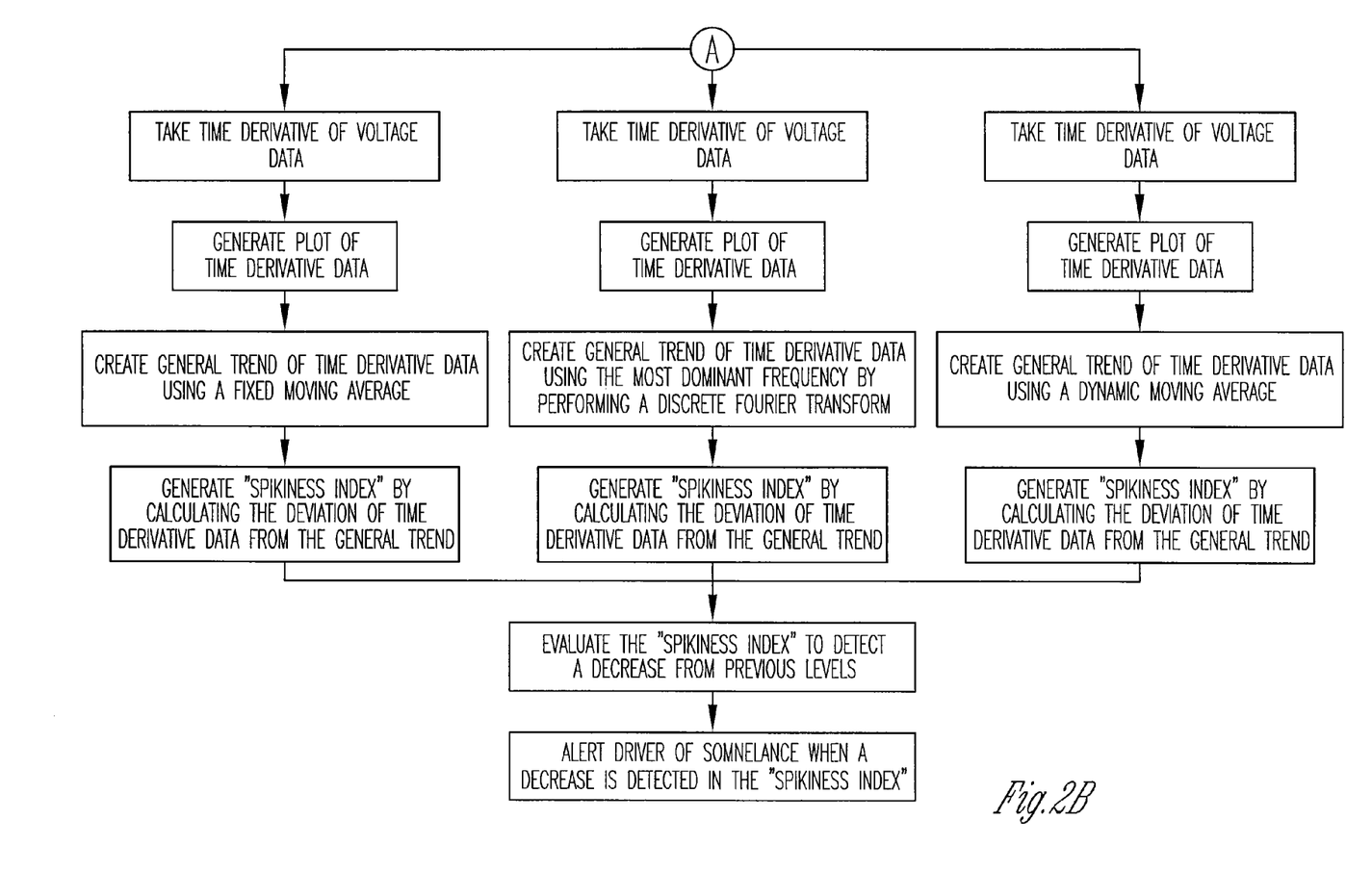

FIG. 2A-B is a block diagram describing the operation of the present invention. The vigilance monitoring system is implemented by selecting one or more of the vehicle-driver interfaces to monitor the state of drowsiness of the driver. The accelerator is the preferred vehicle-driver interface to monitor. The accelerator could also be monitored in conjunction with the steering wheel or brake pedal. Monitoring multiple vehicle-driver interfaces would allow comparison between the two to determine accuracy of each one independent of the other. A sensor is affixed to the desired vehicle-driver interface to monitor the driver's interaction with the chosen vehicle-driver interface. The sensor can be a force sensor or another type of sensor to detect the driver's interaction with the vehicle-driver interface. Present commercially available sensors are small enough to prevent interfering or distracting the driver. One example of a possible force sensor is a force sensitive resistor (FSR) available from Interlink Electronics ("Interlink Electronics,"). The FSR are a polymer thick film (PTR) device which exhibits a decrease in resistance with an increase in the force applied to the active surface. The range of the FSR is from 100 g to 10 kg with a resolution of 0.5% of full scale. The life time of the sensor is more than 10 million actuations. The sensor is insensitive to vibrations and temperature fluctuations and therefore is not affected by vehicle operation and environmental variations. The mechanical response time of the sensor is about 1-2 milli-seconds, which permits a sampling rate of 200 Hz. In the present invention, generally a 10 Hz sampling rate is satisfactory when the accelerator or steering wheel is used to detect driver drowsiness.

The sensor is wired to an intelligent control positioned on the vehicle or a preexisting onboard computer of the vehicle. The signal from the sensor is most often a resistance signal that can be converted to a voltage signal for ease of processing and analyzing. The resistance is converted to voltage using a simple resistance to voltage converter circuit. The force sensitive resistor has a resistance RF and an external resistance RM to control the range of output voltage $V_{out}$, where $V_{out}$ characterizes the force exerted on the accelerator. The intelligent control may also be used to convert the resistance data from the sensor to voltage data for processing using the intelligent control. The voltage data is preferably stored within the intelligent control or an external storage device. One external storage device that can be used to store the voltage data is an ADC card (PCI-DAS6034 from Measurement Computing). The intelligent control is preferably programmed to process the voltage data by taking the time derivatives of the voltage data to represent the voltage data as time derivative data. A plot of the time derivative data may be generated using the intelligent control. In one preferred method of computation, a general trend is modeled of the plot of the time derivative data using a fixed moving average. Another preferred method of computation of the general trend of the plot of the time derivative data uses the most dominant frequency by performing a Discrete Fourier Transform. Still another preferred method of computing the general trend of the time derivative profile uses a dynamic moving average employing square waves for approximating a plot of the time derivative profile. Using the intelligent control, a spikiness index may be generated by calculating the deviation of the time derivative profile from the general trend plot. The level of the spikiness index may be monitored to detect decreases from previous levels indicative of drowsiness or somnolence in the driver. The intelligent control is configured to evaluate the spikiness index, detect drowsiness in the driver and alert the driver of drowsiness.

Another embodiment would entail the acquisition of both force and displacement data in real time by two sensors; one mounted to the steering wheel (positional sensor) and second sensor (force sensor) mounted to the accelerator. To minimize false alarms, such as where the spikiness index or FSD indicates that the driver is drowsy, but in actuality is not drowsy or even failure to detect drowsiness, data may be collected from steering wheel and gas pedal simultaneously. Data from both the steering wheel and accelerator could be used to corroborate against each other for accuracy purposes. Preferably, the force data will be obtained by using a thin film 'force sensing resistor (FSR)', whose electrical resistance changes with applied force. Also, from the steering wheel, driver imparted steering angle rate could be measured with a solid-state gyroscope. Data could be acquired from both gas pedal and steering wheel at a rate of 10 Hz and stored in a data logger. The data could be read from the logger with time stamps. The accelerator data may be processed by taking several orders of derivatives; the same is true for the steering wheel, except the gyroscope data already gives first derivative of the steering angle displacement.

Figure 12:
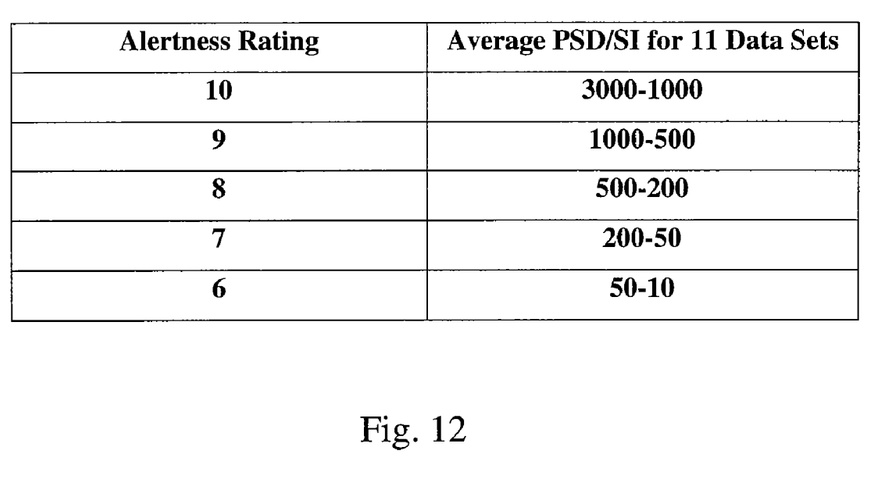
FIG. 12 is table of alertness rating decision module for the present invention.

The time derivatives of the data acquired for each sensor could be fed processed using mathematical model(s) associated with the intelligent control for measuring the spikiness index. The time derivatives could also be computed using a data processing chip. From the time derivative data, the spikiness index or PSD could be computed in real time. The measured spikiness index could then be compared with a 1-10 alertness rating scale to ascertain the alertness of the driver. An alertness rating scale may be established for both steering wheel and accelerator data separately. If both alertness ratings for the steering wheel and accelerator are low, the driver is given warning in various ways depending upon the severity of drowsiness. As shown in FIG. 12, the rating decision module may be arranged to detect onset drowsiness as opposed to later stages of drowsiness. The data in the table of FIG. 12 was developed from the 25 sets of real life data to establish an alertness rating scale from 10-6. In each set, the participant drove more than six hours for at least one session. As shown in FIG. 12 as well, an average driver at very high levels of alertness can have PSD/Spikiness Index (SI) values from 1000 to 2000 units. This is very important information, if one attempts to develop an alertness rating for a statistical population it should be fitted to individual driving styles. One potential alertness rating decision module may be defined by a scale of 1-10 where the 10=excellent, 9=tired but no problem, 8=more tired and somewhat sleepy, 7=sleepy but not willing to stop, 6=sleepy and wished to stop for a break, 5=sleepy, would definitely stop for a break, 4=could drive, but very dangerous to keep on driving, 3=would not drive under any condition, 2=extremely sleepy, 1=unduly impaired. Thus, the module may be configured to detect early stages of drowsiness.

Data Processing and Results

Figure 3:
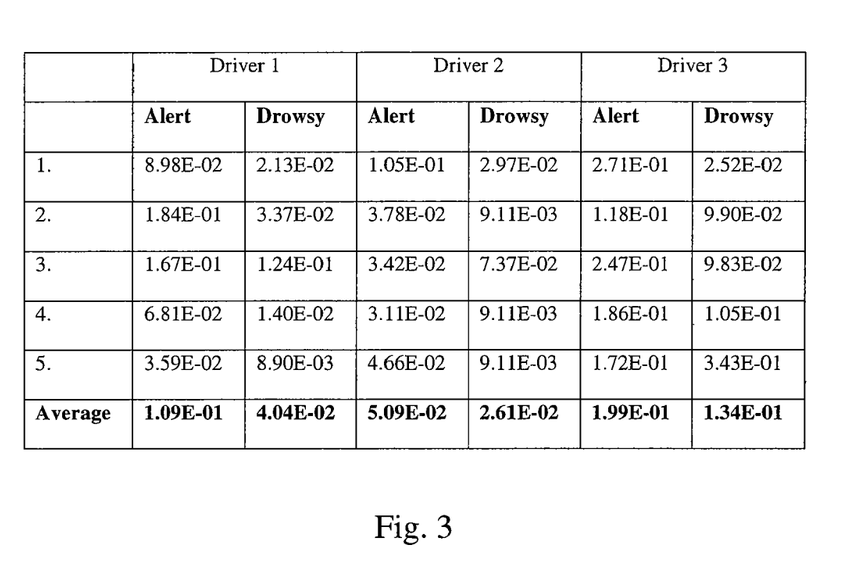
FIG. 3 is a table of the standard deviation for three drivers of the present invention.
Figure 9:
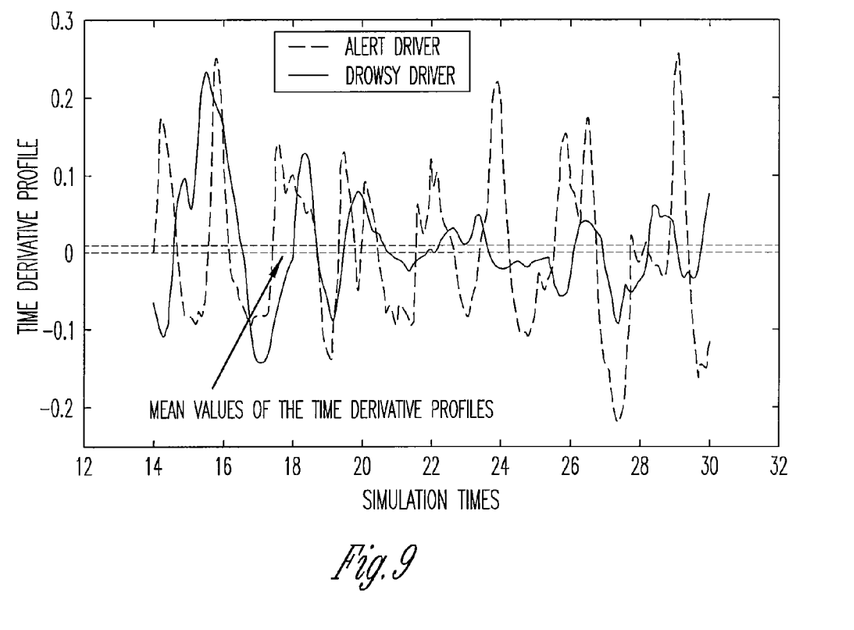
FIG. 9 is a mean value plot of the time derivative profile for the alert and drowsy state of a driver for the present invention.

As previously noted, the spikiness index is used to determine the alertness of the driver. The force data from the sensor is filtered (converted to voltage data) and the time derivative profile is computed by taking time derivatives of the filtered force data. To gain a rough estimate of the deviation of the data, the standard deviation of the data and the results for three drivers was calculated and is tabulated in FIG. 3. The last row in the table is the average of the deviation for the 5 runs of simulation. It can be seen that in all three cases the standard deviation (from mean) is more in case of the alert state of the driver. FIG. 9 shows a plot of the time derivative profile for a small interval of simulation time for one driver (alert and drowsy state) and the mean value of the data (the lower one is for the drowsy state). The standard deviation ($\sigma$) is computed by taking the average of the square of the difference between actual data ($x_i$) and mean ($\mu$) for number of data points.

$$\sigma = \frac{\sum_{i=1}^{n}(x_i - \mu)^2}{n}$$

To compute the spikiness index, i.e. the local deviation of data from the general trend, the deviation from the moving average ($\mu_m$) is calculated. $\mu_m$ is the average of a fixed number of points ($n_{avg} \leq n$) and is equivalent to a local average. Thus, for every point, the deviation from the moving average of the points preceding it (specifically $n_{avg}$ number of points) is computed to estimate the spikiness index. Thus, the spikiness index ($\Psi$), according to deviation from moving average, is given by:

$$\Psi = \frac{\sum_{i=n_{avg}+1}^{n}\left(x_i - \frac{\sum_{j=i-n_{avg}}^{i-1} x_j}{n_{avg}}\right)^2}{n - n_{avg}}$$

Figure 4:
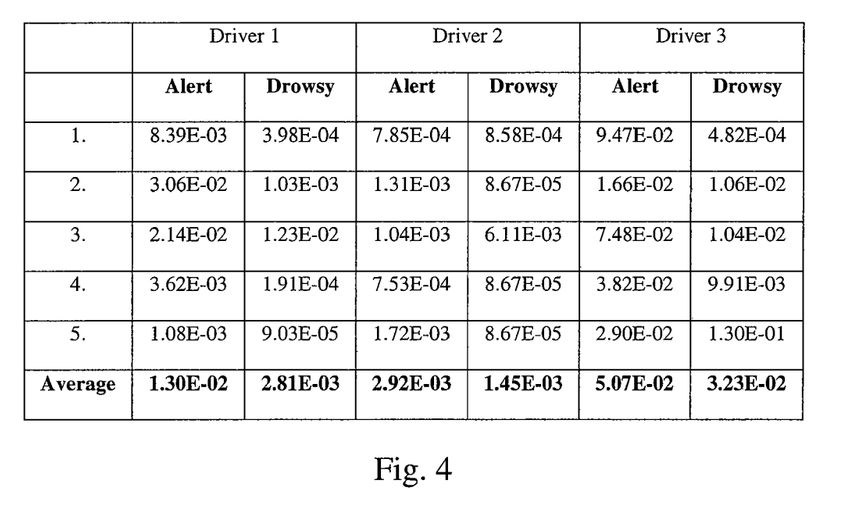
FIG. 4 is a table of the moving average deviation for three drivers of the present invention.
Figure 10:
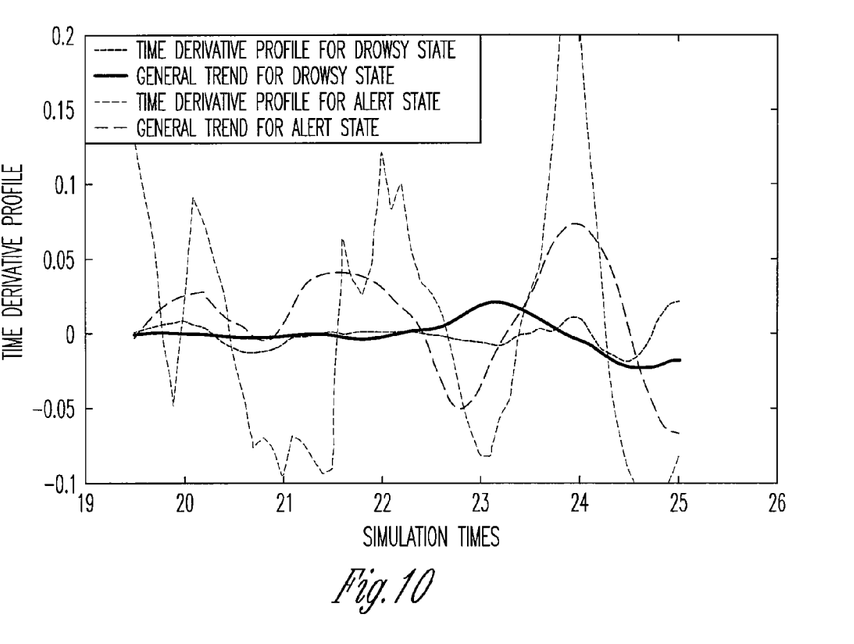
FIG. 10 is a moving average plot of the time derivative profile for the alert and drowsy state of a driver for the present invention.
Figure 11:
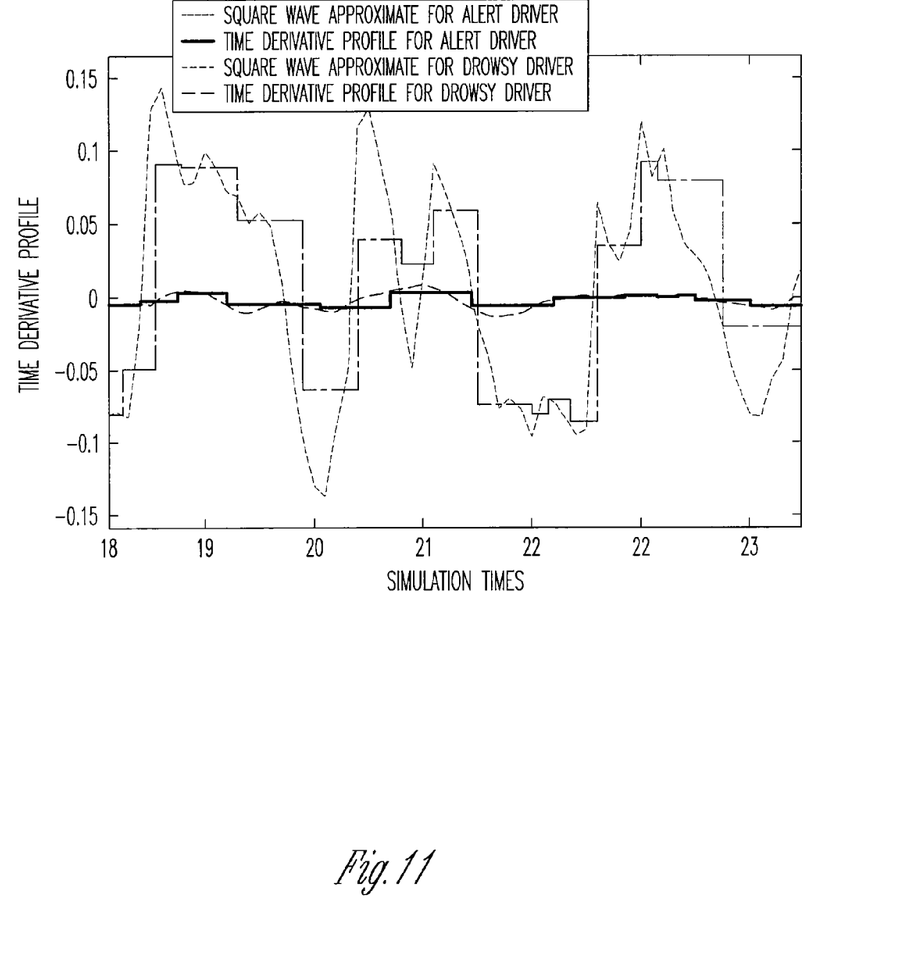
FIG. 11 is an approximated square wave plot of the time derivative profile for the alert and drowsy state of a driver for the present invention.

The spikiness index can be computed using the above equation for all the three drivers (results are tabulated in FIG. 4). It can be seen from the table (last row) that the spikiness index is greater when the driver is alert. The plot of the time derivative profile and the moving average value is shown in FIG. 10. The thinner lines are the time derivative profile for normal and drowsy states of the driver while the thicker lines are the moving average plots. The moving average plots are an indication of the general trend and the deviation of the time derivative profile from this plot is the spikiness index. It should be noted that $n_{avg}$ determines the closeness of the plot to the actual profile; as $n_{avg}$ increases the plot flattens out and eventually becomes a straight line (global mean of the data).

In the above estimation of spikiness index, the number of points to be considered for calculation of the moving average ($n_{avg}$) is fixed. However, other preferred methods of calculating the spikiness index are used since the variation might not be uniform and in some cases $n_{avg}$ might be less or more than desired; this will cause a slightly inaccurate representation of the general trend. One way to circumvent this problem is to perform a DFT (Discrete Fourier Transform) of the data and obtain the most dominant frequency, $f_d$. Thus, $n_{avg} = n/f_d t_s$, will give a reasonable estimate of the desired number of points to be considered for computing the moving average, where $t_s$ is the total simulation time.

Figure 5:
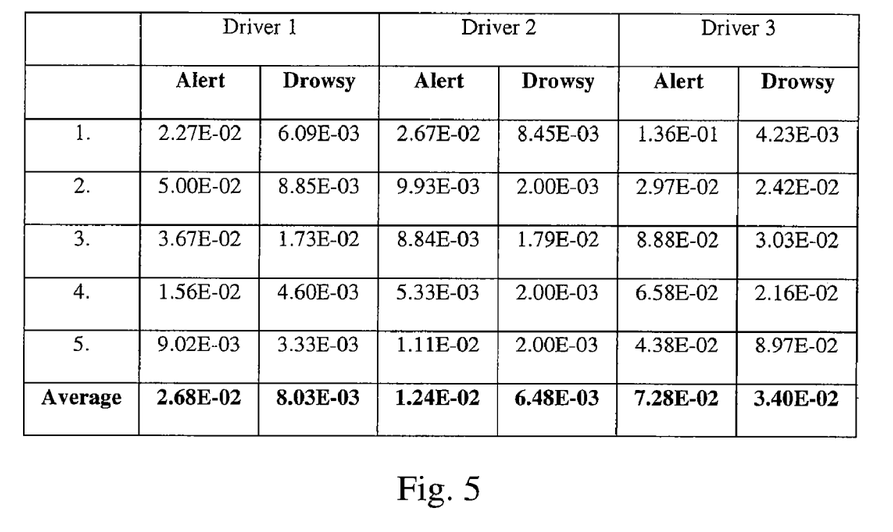
FIG. 5 is a table of the spikiness index for the three drivers of the present invention.
Figure 6:
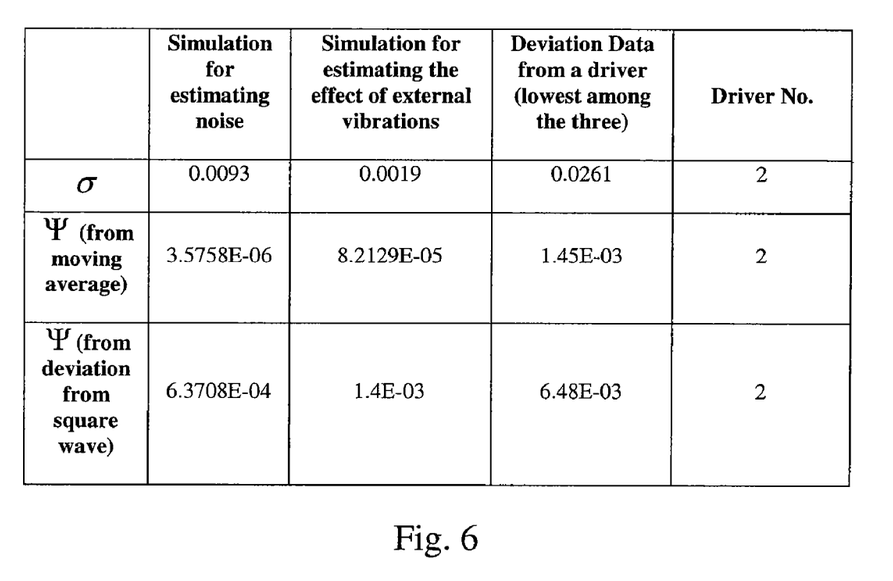
FIG. 6 is a table illustrating the estimated effect of noise and external vibrations on the data of the present invention.

Another way preferred approach is to represent the time derivative profile by an approximate curve and calculate the subsequent deviation of the actual profile from the approximate curve. The approximated curve will follow the actual profile, but will represent the local average of the data. This is similar to the moving average curve, but the number of points for averaging ($n_{avg}$) is dynamic and is chosen such that it captures the variation of time derivative profile to the closest degree. This technique can be used to approximate the time derivative profile by square waves. The deviation of the profile from this approximated curve was calculated to determine the spikiness index, $$\Psi = \frac{\sum_{i=1}^{n}(x_i - \mu_{local})^2}{n}$$

where $\mu_{local}$ is the local average of the data. It should be noted that the square wave is representative of the general trend. The spikiness index was computed using the above method and the results are tabulated in FIG. 5. Again it can be seen that the spikiness index (last row) is more in case of the alert driver. The plot of the time derivative profile along with the approximated square wave (for alert and drowsy states of one driver) is shown in FIG. 6.

An additional metric—the power spectral density of the time derivative data taken from the accelerator or steering wheel—may also be used to measure the level of interaction between the driver and any vehicle-driver interface. The power spectral density which describes how the power (or variance) of a time series is distributed with frequency. If f(t) is a signal, the spectral density $\Phi(\omega)$ of the signal is the square of the magnitude of the continuous Fourier transform of the signal.

$$\Phi(\omega) = \left| \frac{1}{\sqrt{2\pi}} \int_{-\infty}^{\infty} f(t) e^{-i\omega t} dt \right|^2 = \frac{F(\omega) F*(\omega)}{2\pi}$$

where $\omega$ is the angular frequency ($2\pi$ times the cyclic frequency) and $F(\omega)$ is the continuous Fourier transform of f(t).

In order to estimate the effect of noise and external vibrations on the data, two other sets of experiments were performed. To observe the effect of noise, force data was collected for 2 minutes without any force on the accelerator pedal. To investigate the effects of vibration, a 120 psi air compressor was run next to the gas pedal and the sensor input was recorded due to the floor vibration only. In both cases the standard deviation and the spikiness index (computed by both methods) were calculated and compared with the lowest values of the deviations from among the three drivers. The results are tabulated in FIG. 6. The deviation values for the simulation cases of noise and external vibrations are about 10% of the values for simulations of highway driving. Hence the alertness monitoring set-up and algorithm is relatively robust with respect to noise (electronic circuits) and external vibrations.

CONCLUSION

Presented herein is a vigilance monitoring system for characterizing the alertness of the driver by computing the spikiness index of the time derivative profile of the force on a driver-vehicle interface. The system may be easily extended for use with other human-machine interaction interfaces, as well. The present system may also use the spikiness index with Fourier analysis of the time derivative data to obtain a more accurate estimate of the psychological state of the driver, whether drowsy or alert. Moreover, by comparing the data for different levels of vigilance, a rating scale may be developed and statistical analysis may be performed to calculate the level of confidence for the performance of the rating scale. The present vigilance monitoring system may also be assisted by the use of a neural network model, which will be trained with the time derivative profile data so that the model at first 'learns' the driving characteristic of a certain driver at full alertness. The trained model will then be able to detect departure from the normal driving pattern and warn the driver whenever necessary. The present system may employ the time derivative profile data of the gas pedal in conjunction with time derivative profile of steering wheel (frequency and amplitude of rotation of wheel) to enhance the driver vigilance monitoring.

The present invention has been shown and described above with the preferred embodiments, and it is understood that any modifications, substitutions, and additions may be made which are within the intended spirit and scope of the invention. From the foregoing, it can be seen that the present invention accomplishes at least all of its stated objects.

What is claimed is:

1. A vigilance monitoring system for alerting a driver of a vehicle upon detecting a state of drowsiness by calculation of a deviation between a time derivative of force on a driver-vehicle interface and a moving average for the time derivative of force to thereby quantify the state of drowsiness of the driver independent of conditions inside and outside the vehicle, the system comprising:
    a force sensitive resistor connected to at least one driver-vehicle interface to monitor force by the driver on the driver-vehicle interface;
    an intelligent control in communication with the force sensitive resistor;
    a jerk profile modeled from the time derivative of force using the intelligent control;
    a general trend modeled from the moving average of the time derivative of force using the intelligent control; and
    a spikiness index defined by a degree of deviation between the jerk profile and the general trend to thereby quantify the state of drowsiness of the driver independent of conditions inside and outside of the vehicle.

2. The system of claim 1 wherein the driver-vehicle interface comprises an accelerator.

3. The system of claim 1 wherein the moving average is an optimized moving average calculated by a discrete Fourier transform to identify a dominant frequency to thereby assist estimation of an optimum number of points.

4. The system of claim 1 wherein the moving average is a dynamic moving average calculated using a dynamic number of sampling points to approximate the jerk profile with a plurality of square waves.

5. The system of claim 1 wherein the intelligent control alerts the driver of drowsiness upon detection of a decrease in the degree of deviation between the jerk profile and the general trend relative to previous levels.

6. The system of claim 5 further comprises a warning system in communication with the intelligent control, the warning system having an alert tone for notifying the driver of drowsiness.

7. The system of claim 1 further comprises a neural network adapted to receive and store resistance or voltage data from the force sensitive resistor for learning a driving characteristic of the driver while in a state of alertness and detecting a state of drowsiness upon departure from the driving characteristic of the driver in the state of alertness.

8. The system of claim 1 wherein the driver-vehicle interface comprises a steering wheel.

9. The system of claim 1 wherein the driver-vehicle interface comprises both an accelerator and a steering wheel.

10. A method for monitoring and alerting a driver of drowsiness, comprising:
- attaching a sensor to at least one driver-vehicle interface for capturing a force input from the driver on the driver-vehicle interface;
- monitoring the force input from the driver on the at least one driver-vehicle interface;
- calculating a time derivative of the force input on the driver-vehicle interface using force data from the sensor processed by an intelligent control;
- generating a moving average for the time derivative of force on the driver-vehicle interface using the intelligent control;
- monitoring a separation of the time derivative of force and the moving average for the time derivative of force for characterizing drowsiness of the driver independent of road conditions or vehicle behavior; and
- alerting the driver of drowsiness upon detection of a decrease in the separation between the time derivative of force and the moving average.

11. The method of claim 10 wherein the intelligent control further comprises a memory and computational processing chip for storing and processing a voltage output from the sensor.

12. The method of claim 10 further comprising plotting difference values defined by the separation between the time derivative of force and the moving average for providing a spikiness index characterizing driver drowsiness relative to previous levels.

13. The method of claim 12 further comprising using the spikiness index and/or power spectral density for detecting drowsiness in the driver independent of road conditions or vehicle behavior.

14. The method of claim 10 wherein the driver-vehicle interface comprises:
a. a steering wheel;
b. an accelerator; or
c. both a steering wheel and an accelerator.

15. The method of claim 14 further comprising contrasting separation between the time derivative of force and the moving average for the steering wheel and the accelerator.

16. A method for monitoring and alerting a driver of drowsiness in real-time comprising:
- acquiring through a sensor in real-time a driver's force input to a driver-vehicle interface; and
- detecting a decrease in a deviation between:
  a. a time derivative of the driver's force input on the driver-vehicle interface; and
  b. a moving average of the time derivative of the driver's force on the driver-vehicle interface.

17. The method of claim 16 further comprising attaching the sensor to an accelerator and in communication with an intelligent control for recording the driver's force input exerted on the accelerator.

18. The method of claim 17 further comprising attaching another sensor to a steering wheel for recording the driver's force input on the steering wheel.

19. A vigilance monitoring system for alerting a driver of a state of drowsiness comprising:
- a spikiness index defined by a deviation between:
  a. a time derivative of voltage of a sensor at a driver-vehicle interface; and
  b. a moving average of the time derivative of voltage calculated by an intelligent control;
- a resistance sensor having a voltage output response, the resistance sensor connected to the driver-vehicle interface and in communication with the intelligent control; and
- a decrease in the spikiness index relative to previous levels of the spikiness index monitored by the intelligent control to thereby assist in detection of drowsiness of the driver.

20. The system of claim 19 wherein the moving average of the time derivative of voltage is a dynamic moving average for early detection of the state of drowsiness.

* * * * *

UNITED STATES PATENT AND TRADEMARK OFFICE
CERTIFICATE OF CORRECTION

PATENT NO. : 7,663,495 B2  
APPLICATION NO. : 11/548868  
DATED : February 16, 2010  
INVENTOR(S) : Haque et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 502 days.

Signed and Sealed this

Thirtieth Day of November, 2010

David J. Kappos  
*Director of the United States Patent and Trademark Office*